United States Patent
Kim et al.

(10) Patent No.: US 10,261,096 B2
(45) Date of Patent: Apr. 16, 2019

(54) METHOD AND KIT FOR DIAGNOSING DEPRESSION AFTER ACUTE CORONARY SYNDROME USING HOMOCYSTEINE

(71) Applicant: INDUSTRY FOUNDATION OF CHONNAM NATIONAL UNIVERSITY, Gwangju (KR)

(72) Inventors: Jae Min Kim, Gwangju (KR); Hee Ju Kang, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 51 days.

(21) Appl. No.: 15/421,838

(22) Filed: Feb. 1, 2017

(65) Prior Publication Data

US 2018/0059121 A1 Mar. 1, 2018

(30) Foreign Application Priority Data

Aug. 30, 2016 (KR) .................. 10-2016-0110860

(51) Int. Cl.
| | |
|---|---|
| *C07H 21/04* | (2006.01) |
| *C12Q 1/68* | (2018.01) |
| *G01N 33/68* | (2006.01) |
| *C12Q 1/6883* | (2018.01) |
| *B01D 15/08* | (2006.01) |

(52) U.S. Cl.
CPC .......... *G01N 33/6893* (2013.01); *B01D 15/08* (2013.01); *C12Q 1/6883* (2013.01); *G01N 33/6815* (2013.01); *C12Q 2600/118* (2013.01); *C12Q 2600/156* (2013.01); *G01N 2800/304* (2013.01)

(58) Field of Classification Search
None
See application file for complete search history.

(56) References Cited

PUBLICATIONS

Woong-Jang (An association between depression after acute coronary artery syndrome and and methylenetetrahydrofolate reductase gene polymorphism Feb. 2008, Thesis. Provided on IDS). (Year: 2008).*
Nashaat et al. (Egyptian J. of Psychiatry, vol. 33, pp. 83-89, 2012). (Year: 2012).*
Tang et al. (Mol Neurobiol, vol. 53, pp. 2152-2160, May 5, 2015). (Year: 2015).*
Lee et al. (Stress, Brain and Behavior, vol. 5, 1-52, May 16, 2016, p. 43). (Year: 2016).*
Kang et al (Oncotarget, vol. 7, No. 42, pp. 69032-69040, Sep. 10, 2016). (Year: 2016).*
English Translation of Woong-Jang Kim Thesis "An Association between Depression after Acute Coronary Artery Syndrome and Methylenetetrahydrofolate reductase gene polymorphism" Feb. 2008 (Year: 2008).*
Office action dated Sep. 28, 2017 from Korean Patent Office in a counterpart Korean Patent Application No. 10-2016-0110860.
Ys Lee et al., 'Longitudinal Associations of Homocysteine and MTHFR C677T Polymorphism With Depressive Disorder in Patients With Acute Coronary Syndrome', Proceedings of the 23rd Multidisciplinary International Neuroscience and Biological Psychiatry Conference "Stress, Brain and Behavior", pp. 43, vol. 5, 2016.
Woong-Jang Kim , "An association between depression after acute coronary artery syndrome and methylenetetrahydrofolate reductase gene polymorphism", Faculty of Medical Sciences Graduate School Chonnam National University, Gwangju, Korea, pp. 60, Feb. 2008. (English translation of Abstract is submitted herewith.).

* cited by examiner

*Primary Examiner* — Jeanine A Goldberg
(74) *Attorney, Agent, or Firm* — The PL Law Group, PLLC

(57) ABSTRACT

This invention relates to a method of diagnosing the depression, and more particularly to a method and kit for diagnosing depression after acute coronary syndrome, by measuring the concentration of a specific biomarker in the blood of a patient suffering from acute coronary syndrome to predict depression after acute coronary syndrome.

5 Claims, 2 Drawing Sheets

Specification includes a Sequence Listing.

METHOD AND KIT FOR DIAGNOSING DEPRESSION AFTER ACUTE CORONARY SYNDROME USING HOMOCYSTEINE

CROSS-REFERENCE TO RELATED APPLICATION AND CLAIM OF PRIORITY

The present application claims priority to Korean Patent Application KR 10-2016-0110860 filed on Aug. 30, 2016 in the Korea Intellectual Property Office, the disclosures of which are incorporated herein by reference.

BACKGROUND

1. Technical Field

The present invention relates to a method of diagnosing depression, and more particularly to a method and kit for diagnosing depression after acute coronary syndrome, in which the concentration of a specific biomarker in the blood of a patient with acute coronary syndrome is measured to predict depression after acute coronary syndrome (ACS).

2. Description of the Related Art

Homocysteine is an amino acid containing thiol, which is produced via the demethylation of methionine. Homocysteine is metabolized through remethylation. During remethylation, homocysteine is converted into methionine by means of a methionine synthase. As such, vitamin B12 is used as a cofactor, and 5-methyltetrahydrofolate is used as a methyl group donor. Remethylation plays a main role in maintaining the concentration of homocysteine in the blood. Here, 5-methyltetrahydrofolate is prepared from 5,10-methylenetetrahydrofolate by the action of MTHFR (methylenetetrahydrofolate reductase). When the function of MTHFR deteriorates, the amount of the 5-methyltetrahydrofolate cofactor is decreased, whereby remethylation for converting homocysteine into methionine occurs less readily, thus causing hyperhomocysteinemia, in which the blood homocysteine concentration is increased.

A C677T gene mutation of MTHFR, which is the enzyme for controlling the blood homocysteine concentration, results from substituting alanine with valine by converting the $677^{th}$ cytosine into thymine. In particular, the function of MTHFR is known to be decreased by 67.6% in persons having a MTHFR homozygosity mutation, namely 677TT genotype, than in persons of the mutation-free normal 677CC genotype. Therefore, the homozygosity mutation of the MTHFR gene is regarded as a strong factor associated with the onset of hyperhomocysteinemia.

The homocysteine concentration is significantly affected by genetic factors governing methyltetrahydrofolate reductase (MTHFR). Since the 677C→T variant of the MTHFR gene is responsible for thermolabile MTHFR having decreased enzymatic activity, the T allele is associated with high homocysteine concentration. In this regard, the T allele of the MTHFR gene is reported to be associated with an increase in ACS susceptibility upon meta-analysis, and is found to be associated with depression in some research. Specifically, homocysteine may cause atherothrombosis due to a variety of kinds of damage to the blood vascular system, and thus the risk of ACS increases, and furthermore, homocysteine directly suppresses the metabolism of a monoamine neurotransmitter and is thus associated with depression. However, whether homocysteine is a typical biomarker for depression in ACS has not yet been investigated.

SUMMARY

Culminating in the present invention, intensive and thorough research carried out by the present inventors, aiming to solve the problems encountered in the related art, resulted in the finding that blood homocysteine concentration and gene polymorphism are significantly associated with the onset of depression after acute coronary syndrome.

Accordingly, the present invention is intended to provide a method of diagnosing depression after acute coronary syndrome, wherein, based on the results of measurement of homocysteine concentration in the blood of patients with acute coronary syndrome and MTHFR (methylenetetrahydrofolate reductase) gene polymorphism, which has an influence thereon, not only acute depression after acute coronary syndrome but also chronic depression, occurring one year or more subsequent to acute coronary syndrome, may be predicted and diagnosed.

In addition, the present invention is intended to provide a kit for diagnosing depression after acute coronary syndrome, wherein, based on the results of measurement of homocysteine concentration in the blood of patients with acute coronary syndrome and MTHFR gene polymorphism, chronic depression, as well as acute depression after acute coronary syndrome, may be predicted and diagnosed, thus enabling the preemptive prevention of depression in patients and exhibiting clinical usefulness.

The aspects of the present invention are not limited to the foregoing, and other aspects not mentioned herein will be able to be clearly understood to those skilled in the art.

Therefore, the present invention provides a method of diagnosing depression after acute coronary syndrome, comprising: measuring a homocysteine concentration in a blood of a patient with acute coronary syndrome, and determining whether acute depression occurs by comparing the measured homocysteine concentration with a standard concentration.

In a preferred embodiment, the determining comprises diagnosing acute depression when the measured homocysteine concentration is equal to or higher than the standard concentration.

In a preferred embodiment, when the measured homocysteine concentration is equal to or higher than the standard concentration, a likelihood of acute depression occurring is 60% or more.

In a preferred embodiment, when the measured homocysteine concentration is less than the standard concentration, a likelihood of acute depression not occurring is 60% or more.

In a preferred embodiment, the standard concentration is 15.0 µmol or more for 1 L of plasma.

In addition, the present invention provides a method of diagnosing depression after acute coronary syndrome, comprising: measuring a homocysteine concentration in a blood of a patient with acute coronary syndrome, analyzing a methylenetetrahydrofolate reductase (MTHFR) genotype by measuring MTHFR gene polymorphism of the patient, and determining whether chronic depression occurs based on the measured homocysteine concentration and the analyzed MTHFR genotype.

In a preferred embodiment, in the determining, when both a first condition, in which the measured homocysteine concentration is equal to or higher than a standard concentration, and a second condition, in which the analyzed MTHFR genotype of the patient is a MTHFR 677TT genotype, are satisfied, chronic depression is determined to occur.

In a preferred embodiment, the chronic depression includes at least one selected from among incident depressive disorder, which occurs after an acute phase and is present one year after occurrence of acute coronary syndrome, and persistent depressive disorder, which occurs during the acute phase and lasts for one year or more after occurrence of acute coronary syndrome.

In a preferred embodiment, when the first condition and the second condition are satisfied, a likelihood of incident depressive disorder occurring is 39%, and a likelihood of persistent depressive disorder occurring is 70% or more.

In a preferred embodiment, when the first condition and the second condition are not satisfied, a likelihood of incident depressive disorder not occurring is 96%, and a likelihood of persistent depressive disorder not occurring is 73%.

In a preferred embodiment, the standard concentration is 15.0 μmol or more for 1 L of plasma.

In a preferred embodiment, the analyzing the MTHFR genotype comprises isolating DNA including the 677$^{th}$ base of a MTHFR gene separated from the patient, amplifying the isolated DNA using a sense primer and an antisense primer, and checking whether the MTHFR 677TT genotype is present by inspecting the amplified DNA using a restriction enzyme able to recognize a 677C→T mutation.

In addition, the present invention provides a kit for diagnosing depression after acute coronary syndrome, comprising a measurement unit for measuring a plasma homocysteine concentration in the blood of a patient.

In a preferred embodiment, the kit further comprises a genotype analysis unit for checking whether a 677TT genotype is contained by measuring a MTHFR gene polymorphism of the patient.

The present invention has the following superior effects.

In the method of diagnosing depression after acute coronary syndrome according to the present invention, based on the results of measurement of the homocysteine concentration in the blood of patients with acute coronary syndrome and MTHFR (methylenetetrahydrofolate reductase) gene polymorphism, which has an influence thereon, not only acute depression after acute coronary syndrome but also chronic depression occurring one year or more subsequent to acute coronary syndrome can be predicted and diagnosed.

In the kit for diagnosing depression after acute coronary syndrome according to the present invention, based on the results of measurement of the homocysteine concentration in the blood of patients with acute coronary syndrome and MTHFR gene polymorphism, chronic depression, as well as acute depression after acute coronary syndrome, can be predicted and diagnosed, thus enabling the preemptive prevention of depression in patients and exhibiting clinical usefulness.

The aforementioned technical effects of the present invention are not limited to the foregoing, and the effects of the invention that can be recognized by those skilled in the art from the following detailed description even if not explicitly mentioned are also included herein.

BRIEF DESCRIPTION OF THE DRAWING

The above and other features and advantages of the present invention will be more clearly understood from the following detailed description taken in conjunction with the accompanying drawings, in which.

DETAILED DESCRIPTION

Figure 1:
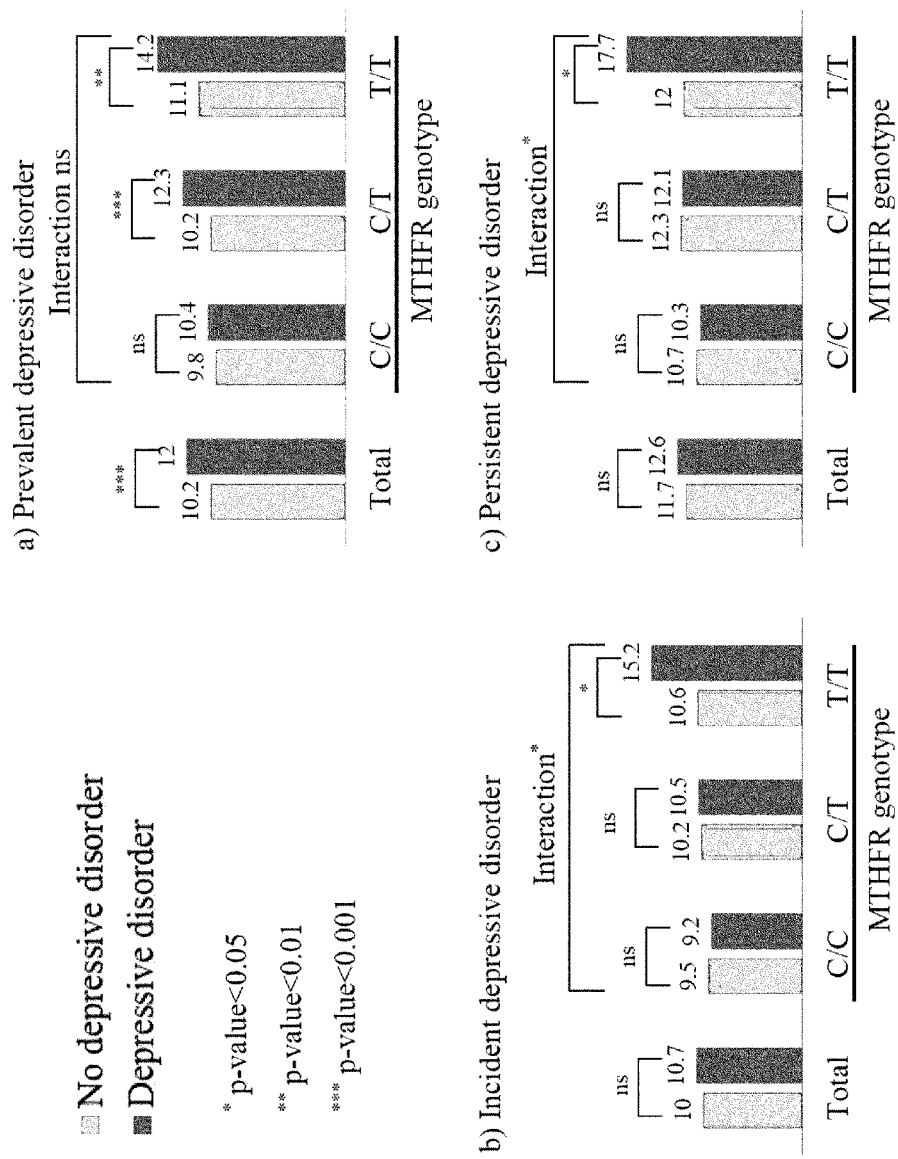
FIG. 1 shows plasma homocysteine concentrations by depressive disorder status and MTHFR genotype.

The terms used herein are merely undertaken to explain specific examples and not to limit the present invention. Unless otherwise stated, the singular expression includes a plural expression. In this application, the terms "include" or "have" are used to designate the presence of features, numbers, steps, operations, elements, parts or combinations thereof described in the specification, and should be understood as not excluding the presence or additional possibility of one or more different features, numbers, steps, operations, elements, parts or combinations thereof.

As used herein, the terms "first", "second", etc. may be used to describe various elements, but these elements should not be limited by these terms. These terms are only used to distinguish one element from another element. For example, the first element may be referred to as a second element or the second element may be referred to as a first element, within the scope of the present invention.

Unless otherwise defined, all of technical or scientific terms used herein have the same meanings as those typically understood by persons having ordinary knowledge in the art to which the present invention belongs.

In interpreting the elements, an error range is to be construed as being included, even if there is no separate description thereof.

For a description of temporal relationships, when the temporal posterior relationship, such as "after", "subsequent to", "following", "before" and so on, is explained, non-continuous cases are also included, so long as "immediately" or "directly" is not used.

The characteristic portions of embodiments of the present invention may be partially or wholly coupled or combined with each other, and a variety of technical operations thereof are possible, and thus the embodiments may be independently or jointly performed.

Hereinafter, a detailed description will be given of preferred embodiments of the present invention with reference to the accompanying drawings.

However, the present invention is not limited to the embodiments described herein but may be embodied into different forms. Throughout the specification, the same reference numerals will refer to the same or like elements.

The present invention addresses a method and kit for diagnosing depression after acute coronary syndrome, wherein the blood homocysteine concentration and MTHFR gene polymorphism are found to be significantly associated with depression after acute coronary syndrome and are thus used as biomarkers in order to predict and/or diagnose not only acute depression but also chronic depression after acute coronary syndrome.

In the method of diagnosing depression after acute coronary syndrome according to the present invention, a first diagnosis method for diagnosing acute depression comprises the steps of measuring the blood homocysteine concentration of a patient with acute coronary syndrome and determining whether acute depression occurs by comparing the measured homocysteine concentration with a standard concentration, and a second diagnosis method for diagnosing chronic depression comprises the steps of measuring the blood homocysteine concentration of a patient with acute coronary syndrome, analyzing the MTHFR genotype by measuring MTHFR gene polymorphism in the patient, and determining whether chronic depression occurs based on the measured homocysteine concentration and the analyzed MTHFR genotype.

The standard concentration may be 12.0 µmol or more for 1 L of plasma, and is preferably 15.0 µmol or more for 1 L of plasma, which is a standard clinical concentration suitable for use in diagnosing hyperhomocysteinemia.

As used herein, the term "acute phase" refers to a period within two weeks after occurrence of acute coronary syndrome, and the term "chronic phase" refers to a period of one year or more after occurrence of acute coronary syndrome, subsequent to the acute phase.

Therefore, acute depression indicates depression that occurs within two weeks after occurrence of acute coronary syndrome, and chronic depression has no temporal relationship with the time of onset of depression, so long as it is associated with acute coronary syndrome, but indicates depression that occurs even one year or more following acute coronary syndrome. Examples of chronic depression may include incident depressive disorder, which is absent during the acute phase but occurs subsequent to the acute phase and is present one year after occurrence of acute coronary syndrome, and persistent depressive disorder, which occurs during the acute stage and lasts for one year or more after occurrence of acute coronary syndrome.

More specifically, the determination step of the first diagnosis method may comprise diagnosing acute depression when the measured homocysteine concentration is equal to or higher than a standard concentration. Based on statistical results that will be described later, when the measured homocysteine concentration is equal to or higher than a standard concentration, the likelihood of acute depression occurring is 60% or more. On the other hand, when the measured homocysteine concentration is less than a standard concentration, the likelihood of acute depression not occurring is 60% or more.

Also, in the determination step of the second diagnosis method, when both a first condition, in which the measured homocysteine concentration is equal to or higher than a standard concentration, and a second condition, in which the analyzed MTHFR genotype of the patient is the MTHFR 677TT genotype, are satisfied, chronic depression is determined to occur. Specifically, when the first condition and the second condition are both satisfied, the likelihood of incident depressive disorder occurring is 39%, and the likelihood of persistent depressive disorder occurring is 70% or more. On the other hand, when the first condition and the second condition are not satisfied, the likelihood of incident depressive disorder not occurring 96%, and the likelihood of persistent depressive disorder not occurring is 73%.

Here, the step of analyzing the genotype may include isolating DNA including the 677$^{th}$ base of the MTHFR gene separated from the patient, amplifying the isolated DNA using a sense primer and an antisense primer, and checking whether the MTHFR 677TT genotype is present by inspecting the amplified DNA using a restriction enzyme able to recognize 677C→T mutation.

In addition, the present invention addresses a kit for diagnosing the onset of depression after acute coronary syndrome, comprising a measurement unit for measuring the plasma homocysteine concentration in the blood of a patient. As necessary, the kit may further include a genotype analysis unit for checking whether the 677TT genotype is contained by measuring the MTHFR genotype of the patient.

In this way, the method and kit for diagnosing depression after acute coronary syndrome according to the present invention are clinically advantageous because at least one of a high blood homocysteine concentration of the patient with acute coronary syndrome and the MTHFR 677TT genotype affects depression after acute coronary syndrome, and particularly, high blood homocysteine concentration is significantly associated with acute depression after acute coronary syndrome, and high blood homocysteine concentration and MTHFR 677TT genotype are significantly associated with chronic depression, thereby predicting depression after acute coronary syndrome and preemptively observing the patient so that depression, which worsens the prognosis of acute coronary syndrome patients, may be treated.

EXAMPLES

1. Subject of Study

The data of the present research were deduced for analysis from larger study named the Korean DEPression in ACS (K-DEPACS) study. The K-DEPACS study was carried out from 2006 to investigate the epidemiology of depression in ACS using observational prospective design. All of the participants were consecutively recruited from patients (N=4809) who were recently hospitalized with ACS at the Department Of Cardiology, Chonnam National University Hospital. The patients were treated based on international guidelines for the management of ACS by the cardiologists who participated in the study. The participants (N=1152) who met the eligibility criteria and agreed to participate in this study were assessed for a depressive disorder diagnosis by the study psychiatrists using the Mini-International Neuropsychiatric Interview (MINI) as in patients within 2 weeks post-ACS, and thereafter as outpatients at intervals of four weeks up to 12 weeks. Among them, 969 patients agreed to blood assay, and comprised the baseline sample. Among 378 patients with depressive disorder in the samples, 255 patients agreed to participate in a 24 week, double-blind and randomized placebo-controlled trial to evaluate the efficacy and safety of escitalopram: EsDEPACS study (Clinical Trial. gov Registry No.: NCT00419471). The first patient was enrolled at May, 2007, and the last patient completed the follow-up evaluation at March, 2013. The evaluation was performed at baseline, 4 weeks, 8 weeks, 12 weeks, 16 weeks, 20 weeks and 24 weeks. Based on the details and main results of this test, escitalopram was found to be superior to placebo in reducing depressive symptoms. The remaining 123 patients who refused to participate in the study were subjected only to conventional ACS medical treatment. All the participants in K-DEPACS and EsDEPACS were approached for a re-examination of depressive status at one year after evaluation at baseline (within two weeks after ACS). Written informed consent was collected for the K-DEPACS and EsDEPACS studies, both of which were approved by the Chonnam National University Hospital Institutional Review Board.

2. Evaluation of Depressive Status

The diagnosis of depressive disorder was performed using the MINI, a structured diagnostic psychiatric interview for DSM-IV, which defines major or minor depressive disorder. The symptom-duration criteria at baseline was within two weeks. Since the number of patients with major depressive disorder was not enough to merit additional analysis, depressive disorder was defined as the combined category of major depressive disorder and minor depressive disorder. Based on the evaluation at two phases (two weeks and one year) after ACS, depressive disorder was classified into acute depression (prevalent depressive disorder), in which depressive disorder was present at baseline, and chronic depression, in which depression was present one year after occurrence of ACS, regardless of the time of onset of depression [incident depressive disorder: cases subsequently occurring in the sample without depressive disorder at baseline, or persistent depressive disorder: cases subsequently occurring in the sample with depressive disorder at baseline].

3. Measurement of Plasma Homocysteine Concentration

Blood was collected from a vein in the upper aim of the patient before breakfast after fasting for 8 hr prior to blood sampling. The whole blood was placed in a vacutainer tube containing trisodium EDTA, cooled with ice, and immediately centrifuged at 2,000 rpm for 5 min to separate plasma, and the collected plasma was stored within 2 hr at −80° C. The total plasma homocysteine concentration was measured using commercially available high-performance liquid chromatography (AxSYM Homocysteine Reagent Pack Abbott, USA).

4. Analysis of MTHFR C677T Polymorphism

DNA isolation was performed from the leukocyte of the blood of a patient using a DNA extraction kit (extraction column, QIAmp blood kit, Qiagen) according to the manufacturer's protocol. The isolated DNA specimen was amplified using a primer set comprising a sense primer (5'-TGAAGGAGAAGGTGTCTGCGGGA(SEQ ID NO 1)-3') and an antisense primer (5'-AGGACGGTGCGGTGAGAGTG(SEQ ID NO 2)-3') by means of a GeneAmp PCR machine (Perkin Elmer 9600). In order to amplify the 198 bp product obtained through the above PCR amplification, a series of processes of denaturation at 95° C. for 60 sec, primer annealing at 62° C. for 90 sec, and primer extension at 72° C. for 60 sec was repeated for 35 cycles. The amplified fragments were digested at 37° C. for 4 hr with a restriction enzyme Hin f1 (10 unit/reaction mixture, available from MBI Fermentas) able to recognize the 677C→T mutation. Thereafter, the Hin f1-treated fragments were electrolyzed with polyacryl amide gel and then stained with EtBr (ethidium bromide) to observe the mutation status.

5. Demographic and Clinical Covariates

The characteristics of factors that confound or mediate the association between depressive disorder and ACS were evaluated at baseline. The data for age, gender, education, living status (living alone or not), housing (own or rent), current occupation (currently employed or not), and previous and family histories of depression were obtained. The following cardiovascular risk factors were checked: previous and family histories of ACS, diagnosed hypertension and diabetes, hypercholesterolemia based on fasting serum total cholesterol level (200 mg/dL), obesity measured by body mass index (BMI), and current smoking habits. In order to measure the current cardiac status, the severity of ACS was estimated by the Killip classification, the left ventricular ejection fraction (LVEF) was estimated using echocardiography, and serum cardiac biomarkers, such as troponin I and creatine kinase-MB (CK-MB), were measured. Other factors able to affect the homocysteine concentration, such as serum creatinine level and vitamin supplement, were taken into consideration.

6. Statistical Analysis

Demographic and clinical characteristics were compared between patients with and without depressive disorder at baseline using t-tests or chi-squared ($\chi^2$) tests, as appropriate. The characteristics significantly associated with depressive disorder (p<0.05) were used as covariates in other regression models. In the first analysis, plasma homocysteine was regarded as a continuous value. The homocysteine concentration and the MTHFR C677T gene polymorphism were compared between patients with and without prevalent/incident/persistent depressive disorder using t-tests and $\chi^2$ tests, respectively. Odds ratios (ORs) for depressive status were estimated using a logistic regression model after adjustment for relevant covariates. In order to evaluate the effects of potential interactions of homocysteine concentration and MTHFR C677T polymorphism on depressive status, the following analyses were performed: i) the homocysteine concentration values were compared between genotypes using ANOVA; ii) the association between homocysteine concentration and depressive status was assayed in each genotype; and iii) the bidirectional interaction between homocysteine concentration and genotype was tested using a multivariate regression model. Additional analysis was performed in the same manner as above in order to investigate the association of clinically significant categories of hyperhomocysteinemia, defined by a plasma level of 15.0 μmol/L or more. Also, diagnostic statistics, for example, sensitivity, specificity, positive predictive value (PPV) and negative predictive value (NPV), were calculated for the status of depressive disorder. Also, sensitivity analysis was performed in the same manner as above under the condition that participants with a previous history of depression were excluded. The statistical analysis was conducted using SPSS 18.0 software.

7. Results (1) Demographic and Clinical Characteristics of All Participants

Among 969 participants, 378 participants suffered from prevalent depressive disorder (major or minor) [39.0%; major and minor depressive disorder were 177 (18.3%) and 201 (20.7%), respectively]. The baseline demographic and clinical characteristics affecting prevalent depressive disorder were shown in Table 1 below. Prevalent depressive disorder (depressive disorder at baseline) was significantly associated with females, low education, living alone, rental housing, currently unemployed, high HAMD score, the presence of hypertension and diabetes, and current smoking habits.

TABLE 1

| | No depressive disorder (N = 591) | Depressive disorder (N = 378) | Statistical coefficient | p-value* |
|---|---|---|---|---|
| Socio-demographic characteristics | | | | |
| Age, mean (SD) years | 57.7 (11.3) | 59.0 (10.8) | t = −1.860 | 0.063 |
| Gender, N (%) female | 118 (20.0) | 151 (39.9) | $\chi^2$ = 45.90 | <0.001 |
| Education, mean (SD) years | 10.2 (4.8) | 9.3 (4.4) | t = +3.013 | 0.003 |
| Living alone, N (%) | 47 (8.0) | 45 (11.9) | $\chi^2$ = 4.191 | 0.041 |
| Housing, N (%) rented | 73 (12.4) | 77 (20.4) | $\chi^2$ = 11.33 | 0.001 |
| Currently unemployed, N (%) | 192 (32.5) | 176 (46.6) | $\chi^2$ = 19.39 | <0.001 |

TABLE 1-continued

|  | No depressive disorder (N = 591) | Depressive disorder (N = 378) | Statistical coefficient | p-value* |
|---|---|---|---|---|
| Depression characteristics | | | | |
| Previous depression, N (%) | 17 (2.9) | 17 (4.5) | $\chi^2 = 1.789$ | 0.181 |
| Family history of depression, N (%) | 11 (1.9) | 12 (3.2) | $\chi^2 = 1.716$ | 0.190 |
| HAMD, mean (SD) score | 3.6 (2.7) | 14.2 (5.0) | $t = -38.09$ | <0.001 |
| Cardiac risk factors, N (%) | | | | |
| Previous ACS | 20 (3.4) | 19 (5.0) | $\chi^2 = 1.610$ | 0.205 |
| Family history of ACS | 15 (2.5) | 16 (4.2) | $\chi^2 = 2.138$ | 0.144 |
| Hypertension | 252 (42.6) | 206 (54.5) | $\chi^2 = 13.01$ | <0.001 |
| Diabetes mellitus | 93 (15.7) | 98 (25.9) | $\chi^2 = 15.13$ | <0.001 |
| Hypercholesterolemia | 296 (50.1) | 190 (50.3) | $\chi^2 = 0.003$ | 0.956 |
| Obesity | 259 (43.8) | 156 (41.3) | $\chi^2 = 0.614$ | 0.433 |
| Current smoker | 249 (42.1) | 117 (31.0) | $\chi^2 = 12.26$ | <0.001 |
| Current cardiac status | | | | |
| Killip class >1, N (%) | 97 (16.4) | 71 (18.8) | $\chi^2 = 0.904$ | 0.342 |
| LVEF, mean (SD) % | 61.4 (11.2) | 60.8 (11.4) | $t = +0.772$ | 0.440 |
| Troponin I, mean (SD) mg/dL | 9.9 (16.6) | 9.9 (11.8) | $t = +0.063$ | 0.949 |
| CK-MB, mean (SD) mg/dL | 17.6 (41.1) | 17.1 (30.4) | $t = +0.178$ | 0.858 |
| Other factors | | | | |
| Creatinine, mean (SD) mg/dl | 0.9 (0.3) | 0.9 (0.3) | $t = +1.013$ | 0.462 |
| Vitamin supplement, N (%) | 13 (2.2) | 10 (2.6) | $\chi^2 = 0.198$ | 0.657 |

*p-values using t-tests or $\chi^2$ tests as appropriate.
HAMD, Hamilton Depression Rating Scale; ACS, acute coronary syndrome; LVEF, left ventricular ejection fraction; CK-MB, Creatine kinase-MB.

(2) Analysis of Association of Homocysteine Concentration and MTHFR Gene Polymorphism with Status of Depressive Disorder at Baseline and at Follow-Up Among all 969 participants at baseline, 711 participants (73.4%) were successfully followed. The remaining 258 participants lost to follow up, were older and had higher Killip class (p<0.05) than the participants who were subjected to follow-up observation. Among the 426 participants not suffering from depressive disorder at baseline, the number of patients with incident depressive disorder, i.e. who were observed to have depressive disorder at follow-up was 53 (12%), and 130 patients (46%) among the 285 participants suffering from depressive disorder at baseline were observed to have persistent depressive disorder, in which depressive disorder was still present even at follow-up.

In order to analyze the association of homocysteine concentration and MTHFR gene polymorphism with the status of acute depression and chronic depression, the plasma homocysteine concentration and MTHFR gene polymorphism were analyzed from the blood of ACS patients only at baseline. The depressive status of patients based on the evaluation at baseline and follow-up was classified into acute depression, that is, prevalent depressive disorder, and chronic depression, that is, incident depressive disorder and persistent depressive disorder, and, depending on the status of each kind of depressive disorder, the association of the analyzed MTHFR genotype and the measured plasma homocysteine concentration were analyzed. The results are shown in FIG. 1 and Tables 2 and 3 below.

With reference to FIG. 1, the numeral data indicate plasma homocysteine concentration (μmol/L). Depending on the presence or absence of depressive disorder, p-values were deduced using a logistic regression test after adjustment for gender, education, living status, housing type, current employment status, hypertension, diabetes, current smoking habits (prevalent depressive disorder and incident depressive disorder) and treatment status (persistent depressive disorder). The interaction between the homocysteine concentration and the MTHFR genotype on the depressive status was deduced from the same adjusted model. In Tables 2 and 3, p-values resulted from t-tests or $\chi^2$ tests.

TABLE 2

|  | Prevalent depressive disorder at 2 weeks after ACS | | | Incident depressive disorder at 1 year after ACS | | | Persistent depressive disorder at 1 year after ACS | | |
|---|---|---|---|---|---|---|---|---|---|
|  | Absent (N = 591) | Present (N = 378) | p-value | Absent (N = 373) | Present (N = 53) | p-value | Absent (N = 155) | Present (N = 130) | p-value |
| Homocysteine, mean (SD) μmol/l | 10.2 (3.7) | 12.0 (5.1) | <0.001 | 10.0 (3.7) | 10.7 (4.3) | 0.269 | 11.7 (4.8) | 12.6 (5.9) | 0.157 |
| MTHFR genotype, N (%) | | | | | | | | | |
| C/C | 214 (36.2) | 128 (33.9) | 0.749 | 136 (36.5) | 18 (34.0) | 0.740 | 51 (32.9) | 41 (31.5) | 0.882 |
| C/T | 277 (46.9) | 185 (48.9) | | 177 (47.5) | 28 (52.8) | | 73 (47.1) | 65 (50.0) | |

TABLE 2-continued

|  | Prevalent depressive disorder at 2 weeks after ACS | | | Incident depressive disorder at 1 year after ACS | | | Persistent depressive disorder at 1 year after ACS | | |
| --- | --- | --- | --- | --- | --- | --- | --- | --- | --- |
|  | Absent (N = 591) | Present (N = 378) | p-value | Absent (N = 373) | Present (N = 53) | p-value | Absent (N = 155) | Present (N = 130) | p-value |
| T/T | 100 (16.9) | 65 (17.2) |  | 60 (16.1) | 7 (13.2) |  | 31 (20.0) | 24 (18.5) |  |

TABLE 3

|  | Homocysteine concentration | | MTHFR genotype | | Homocysteine concentration X MTHFR genotype | |
| --- | --- | --- | --- | --- | --- | --- |
|  | Wald | OR (95% CI) | Wald | OR (95% CI) | Wald | OR (95% CI) |
| Prevalent depressive disorder[a] | 30.63 | 1.11 (1.07-1.15)*** | 0.14 | 0.96 (0.79-1.18) | 1.19 | 1.03 (0.98-1.08) |
| Incident depressive disorder[a] | 0.51 | 1.03 (0.95-1.11) | 0.05 | 0.95 (0.62-1.47) | 3.65 | 1.10 (1.00-1.20)* |
| Persistent depressive disorder[b] | 1.13 | 1.04 (0.99-1.09) | 0.17 | 0.93 (0.65-1.32) | 3.90 | 1.12 (1.02-1.23)* |

[a]adjusted for gender, education, living alone, housing, current employment, hypertension, diabetes, and current smoking
[b]adjusted for the same model as in prevalent depressive disorder plus treatment status (escitalopram, placebo, and medical treatment only)
*p-value <0.05,
**p-value <0.01,
***p-value <0.001

As is apparent from FIG. 1 and Tables 2 and 3, considerably high homocysteine concentration was significantly associated with acute depression, namely prevalent depressive disorder, but was not significantly associated with chronic depression, namely incident depressive disorder and persistent depressive disorder. In the case of the MTHFR genotype, no deviation from Hardy-Weinberg equilibrium was observed (p-value=0.673). Also, no significant associations were found for MTHFR genotype with any depressive disorder (all p-values >0.7). In order to evaluate whether the homocysteine concentration and the MTHFR genotype are associated with depressive status, logistic regression analysis was performed after adjustment for covariates, whereby similar results were obtained.

As for the interaction of homocysteine concentration and MTHFR genotype depending on the depressive status, FIG. 1 shows the results of comparison of homocysteine concentrations depending on the status of depressive disorder in each genotype. The higher homocysteine concentration was associated with prevalent depressive disorder in the presence of the C/T and T/T genotypes, and with incident depressive disorder and persistent depressive disorder only in the presence of the T/T genotype. The interactions between genotype and raised homocysteine in logistic regression models after adjustment for covariates are summarized in Table 3. Although an important interaction between homocysteine concentration and the MTHFR genotype was found in incident depressive disorder and persistent depressive disorder, it was not found in prevalent depressive disorder.

Figure 2:
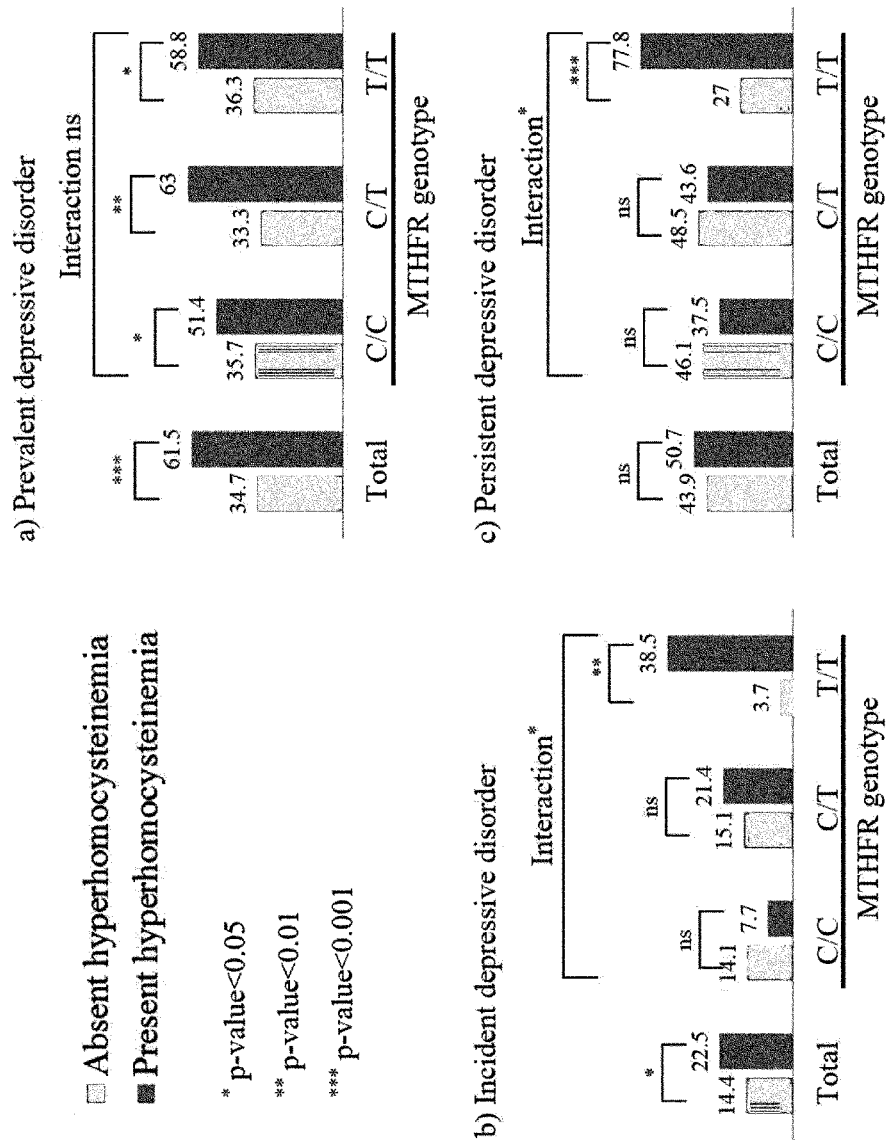
FIG. 2 shows depressive disorder status by hyperhomocysteinemia and MTHFR genotype.

(3) Analysis of Association of Clinical Hyperhomocysteinemia and MTHFR Gene Polymorphism with the Status of Depressive Disorder The prevalence rate of hyperhomocysteinemia was 16.1% (156 of 969 participants), and association with depressive status is illustrated in FIG. 2. In all samples, hyperhomocysteinemia was significantly associated with prevalent depressive disorder (sensitivity of 64%, and specificity of 63%) and incident depressive disorder, but not with persistent depressive disorder. Upon analysis based on the MTHFR genotype, hyperhomocysteinemia was significantly associated with prevalent depressive disorder in the presence of C/T and T/T genotypes, and hyperhomocysteinemia was associated with incident depressive disorder and persistent depressive disorder in the presence of the T/T genotype (PPV and NPV for incident depressive disorder were 39% and 96%, respectively, and PPV and NPV for persistent depressive disorder were 78% and 73%, respectively). Based on the results of analysis of logistic regression after adjustment for covariates, an important interaction between hyperhomocysteinemia and genotype was found in incident depressive disorder (p-value=0.030) and persistent depressive disorder (p-value=0.027), but was not found in prevalent depressive disorder (p-value=0.243).

Such test results support a crucial role of homocysteine in the pathogenesis of depressive disorder comorbid with ACS independently at acute phase and interactively with MTHFR genotype at chronic phase. Thus, plasma homocysteine analysis, especially clinical hyperhomocysteinemia analysis, makes it possible to screen the risk group of depressive disorder in the acute phase of ACS, whereby appropriate treatment may be applied and which is thus clinically useful.

Furthermore, depression in ACS leads to a very high disease burden and is difficult to treat. According to the present invention, assaying homocysteine and MTHFR genotype may allow more focused interventions for the prevention of management of depressive disorder in the susceptible sub-group for depressive disorder not only in the acute phase of ACS but also in the chronic phase of ACS. Therefore, the present invention is useful in the prevention or preemptive treatment of early-stage depression after ACS and/or before the onset of depression.

Although the preferred examples and test examples of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for diagnosing and treating a patient with chronic depression after acute coronary syndrome, comprising:
 a) measuring a homocysteine concentration in a blood sample from the patient with acute coronary syndrome and comparing the measured homocysteine concentration with the standard concentration of 15.0 umol for 1 L of plasma;
 b) analyzing the methylenetetrahydrofolate reductase (MTHFR) genotype at position 677; and
 c) detecting both a homocysteine concentration equal to or higher than the standard concentration and a MTHFR 677TT genotype in the patient;
 d) diagnosing the patient with chronic depression; and
 e) administering an antidepressant to the patient diagnosed with the chronic depression thereby treating the chronic depression.

2. The method of claim 1, wherein the chronic depression includes at least one selected from among incident depressive disorder, which occurs after an acute phase and is present one year after occurrence of acute coronary syndrome, and persistent depressive disorder, which occurs during the acute phase and lasts for one year or more after occurrence of acute coronary syndrome.

3. The method of claim 2, wherein the analyzing the MTHFR genotype comprises isolating DNA including a $677^{th}$ base of a MTHFR gene separated from the patient, amplifying the isolated DNA using a sense primer and an antisense primer, and checking whether the MTHFR 677TT genotype is present by inspecting the amplified DNA using a restriction enzyme able to recognize a 677C→T mutation.

4. The method of claim 1, wherein the analyzing the MTHFR genotype comprises isolating DNA including a $677^{th}$ base of a MTHFR gene separated from the patient, amplifying the isolated DNA using a sense primer and an antisense primer, and checking whether the MTHFR 677TT genotype is present by inspecting the amplified DNA using a restriction enzyme able to recognize a 677C→T mutation.

5. The method of claim 1, wherein the antidepressant is escitalopram.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: sense primer

<400> SEQUENCE: 1
tgaaggagaa ggtgtctgcg gga                                    23

<210> SEQ ID NO 2
<211> LENGTH: 20
<212> TYPE: DNA
<213> ORGANISM: Artificial Sequence
<220> FEATURE:
<223> OTHER INFORMATION: antisense primer

<400> SEQUENCE: 2
aggacggtgc ggtgagagtg                                        20